US009636256B2

(12) United States Patent
Hegels

(10) Patent No.: US 9,636,256 B2
(45) Date of Patent: May 2, 2017

(54) METHOD AND APPARATUS FOR CALCULATING A LASER SHOT FILE FOR USE IN AN EXCIMER LASER

(71) Applicant: Technolas Perfect Vision GmbH, Munich (DE)

(72) Inventor: Ernst Hegels, Kirchheim (DE)

(73) Assignee: TECHNOLAS PERFECT VISION GMBH, Munich (DE)

( * ) Notice: Subject to any disclaimer, the term of this patent is extended or adjusted under 35 U.S.C. 154(b) by 95 days.

(21) Appl. No.: 14/134,541

(22) Filed: Dec. 19, 2013

(65) Prior Publication Data

US 2015/0173946 A1  Jun. 25, 2015
US 2016/0346120 A9  Dec. 1, 2016

Related U.S. Application Data

(63) Continuation of application No. 12/375,428, filed as application No. PCT/EP2007/057782 on Feb. 27, 2007, now abandoned.

(51) Int. Cl.
| | | |
|---|---|---|
| A61B 18/20 | (2006.01) | |
| A61F 2/14 | (2006.01) | |
| A61F 2/16 | (2006.01) | |
| A61F 9/008 | (2006.01) | |
| B23K 26/38 | (2014.01) | |

(52) U.S. Cl.
CPC ........ *A61F 9/0084* (2013.01); *A61F 9/00812* (2013.01); *B23K 26/38* (2013.01); *A61F 9/00814* (2013.01); *A61F 2009/00878* (2013.01)

(58) Field of Classification Search
CPC .. A61F 9/008; A61F 9/00802; A61F 9/00804; A61F 9/0081; A61F 2009/00872; A61F 2009/00878; A61F 2009/00888; A61F 2/14; A61F 2/11; A61F 2/142; A61F 2/145; A61F 2/147; A61F 2/16; A61F 2/1613; A61F 2/1602; A61F 2/1629
USPC ............. 606/4–6, 10–12; 623/4.1, 5.11, 6.11
See application file for complete search history.

(56) References Cited

U.S. PATENT DOCUMENTS

| | | | |
|---|---|---|---|
| 5,425,727 A | 6/1995 | Koziol | |
| 5,777,719 A | 7/1998 | Williams | |
| 5,891,132 A | 4/1999 | Hohla | |
| 5,928,221 A | 7/1999 | Sasnett | |

(Continued)

FOREIGN PATENT DOCUMENTS

| | | |
|---|---|---|
| DE | 19727573 | 5/1998 |
| DE | 20 2005 018911 | 3/2006 |

(Continued)

OTHER PUBLICATIONS

US 5,423,802, 06/1995, Marshall (withdrawn)

(Continued)

*Primary Examiner* — Ahmed Farah
(74) *Attorney, Agent, or Firm* — Thompson Hine LLP

(57) ABSTRACT

The invention relates to a method and apparatus for calculating a laser shot file for use in an excimer laser comprising the steps of providing information with respect to a desired ablation profile, calculating the shot density of the desired ablation profile, using a cost function for placing laser shots of the excimer laser on grid positions wherein a threshold value is determined based on the calculated shot density of the desired ablation profile.

15 Claims, 8 Drawing Sheets

(56) References Cited

U.S. PATENT DOCUMENTS

| | | |
|---|---|---|
| 5,949,521 A | 9/1999 | Williams |
| 5,984,916 A | 11/1999 | Lai |
| 6,033,075 A | 3/2000 | Fujieda |
| 6,086,204 A | 7/2000 | Magnante |
| 6,090,100 A * | 7/2000 | Hohla .................. A61F 9/008 606/10 |
| 6,095,651 A | 8/2000 | Williams |
| 6,132,424 A | 10/2000 | Tang |
| 6,159,205 A | 12/2000 | Woodward et al. |
| 6,271,936 B1 | 8/2001 | Yu et al. |
| 6,325,792 B1 | 12/2001 | Swinger |
| 6,332,216 B1 | 12/2001 | Manjunath |
| 6,394,999 B1 | 5/2002 | Williams |
| 6,413,251 B1 | 7/2002 | Williams |
| 6,454,761 B1 | 9/2002 | Freedman |
| 6,500,171 B1 | 12/2002 | Williams |
| 6,508,812 B1 | 1/2003 | Williams |
| 6,511,180 B2 | 1/2003 | Guirao et al. |
| 6,607,521 B2 | 8/2003 | Vinciguerra |
| 6,635,051 B1 | 10/2003 | Hohla |
| 6,715,877 B2 | 4/2004 | Molebny |
| 6,755,819 B1 | 6/2004 | Waelti |
| 6,808,266 B2 | 10/2004 | Youssefi et al. |
| 6,848,790 B1 | 2/2005 | Dick |
| 6,923,802 B2 | 8/2005 | Williams |
| 6,997,555 B2 | 2/2006 | Dick |
| 7,380,942 B2 | 6/2008 | Molebny |
| 2002/0026180 A1 | 2/2002 | Nakamura |
| 2002/0075451 A1 | 6/2002 | Ruiz |
| 2002/0082629 A1 | 6/2002 | Cox |
| 2003/0023233 A1* | 1/2003 | Smith .................. A61F 9/008 606/5 |
| 2003/0048413 A1 | 3/2003 | Ross |
| 2003/0128335 A1 | 7/2003 | Campin |
| 2003/0193647 A1 | 10/2003 | Neal |
| 2004/0002697 A1 | 1/2004 | Youssefi et al. |
| 2004/0021874 A1 | 2/2004 | Shimmick |
| 2005/0159733 A1 | 7/2005 | Dick |
| 2005/0273088 A1 | 12/2005 | Youssefi et al. |
| 2008/0033408 A1 | 2/2008 | Bueler |
| 2008/0058780 A1 | 3/2008 | Vogler |
| 2009/0264874 A1* | 10/2009 | Hegels .................. A61F 9/008 606/5 |
| 2009/0306635 A1* | 12/2009 | Hegels .................. A61F 9/008 606/5 |
| 2011/0276043 A1* | 11/2011 | Youssefi .................. A61F 9/008 606/5 |

FOREIGN PATENT DOCUMENTS

| | | |
|---|---|---|
| DE | 10 2005 006897 | 8/2006 |
| EP | 0697611 | 2/1996 |
| EP | 1396244 A2 | 3/2004 |
| EP | 1719483 | 11/2006 |
| JP | 2000300596 | 10/2000 |
| JP | 2002524144 | 8/2002 |
| WO | 9527535 | 10/1995 |
| WO | 9611655 | 4/1996 |
| WO | 9848746 | 11/1998 |
| WO | 0124688 | 4/2001 |
| WO | 0124688 A | 4/2001 |
| WO | 0128410 A | 4/2001 |
| WO | 0128477 A1 | 4/2001 |
| WO | 0234178 | 5/2002 |
| WO | 03068103 | 8/2003 |
| WO | 03075778 | 9/2003 |
| WO | 2004041104 | 5/2004 |
| WO | 2004052253 A1 | 6/2004 |
| WO | 2004053568 | 6/2004 |
| WO | 2004095187 | 11/2004 |
| WO | 2004095187 A | 11/2004 |
| WO | 2005007002 | 1/2005 |
| WO | 2007012924 | 2/2007 |
| WO | 2007143111 | 12/2007 |

OTHER PUBLICATIONS

International Search Report, International App. No. PCT/EP2007/057782, date of mailing Oct. 26, 2007.

Damien Gatinel, et al., "Three-dimensional representation and qualitative comparisons of the amount of tissue ablation to treat mixed and compound astigmatism," Journal of Cataract and Refractive Surgery, vol. 28 (No. 11), p. 2026-2034 (Nov. 1, 2002).

* cited by examiner

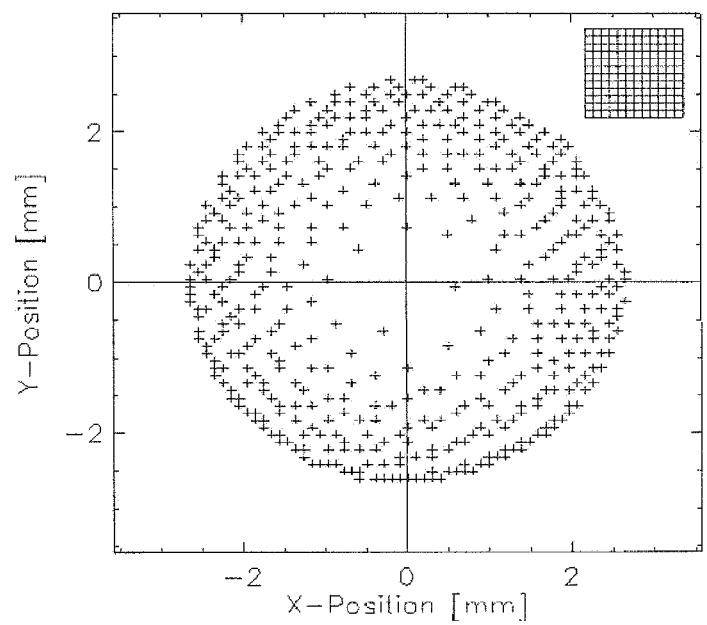
Figure 1A: An ablation was calculated using a constant threshold.

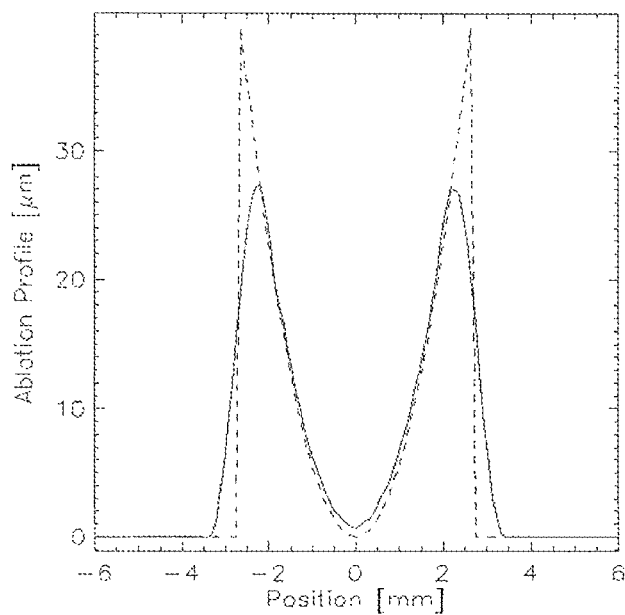
Figure 1B: Cross-Section along the horizontal axis of Fig 1A.

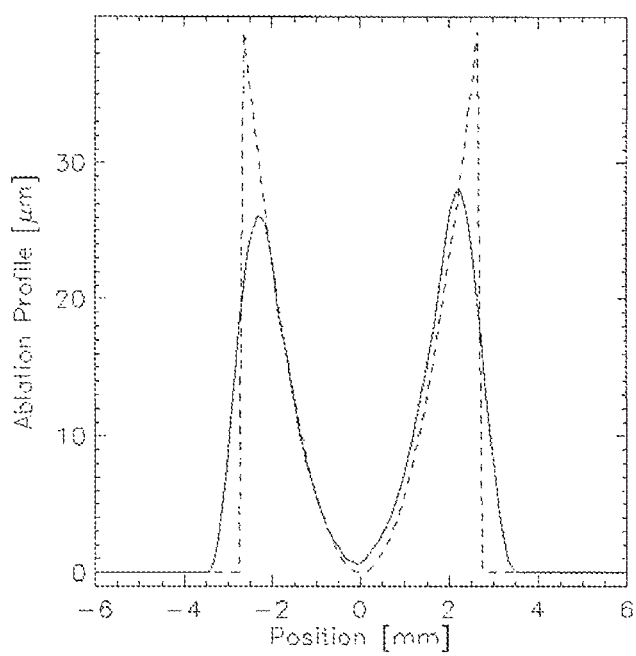
Figure 1C: Cross-Section along the vertical axis of Fig. 1A.

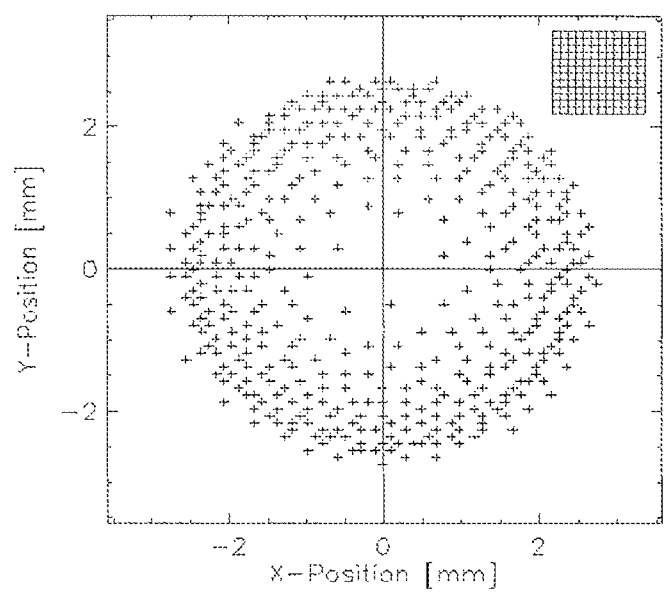
Figure 2A: An ablation was calculated using a dynamic threshold.

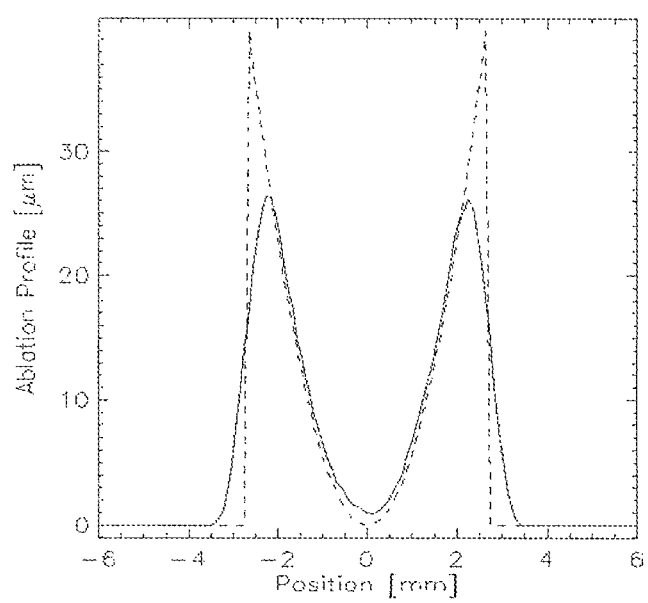
Figure 2B: Cross-Section along the horizontal axis of Fig. 2A.

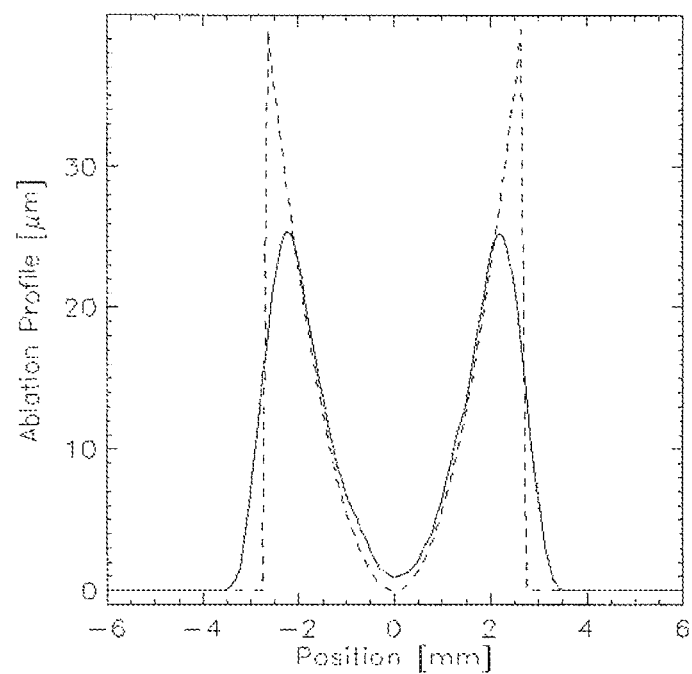
Figure 2C: Cross-Section along the vertical axis of Fig. 2A.

|  |  |  |  |  |  |  |
|---|---|---|---|---|---|---|
|  |  |  |  |  |  |  |
|  |  |  |  |  |  |  |
|  |  |  |  |  |  |  |
| 2.667 | 4.000 | 8.000 | Active position |  |  |  |
| 2.530 | 3.578 | 5.657 | 8.000 | 5.657 | 3.578 | 2.530 |
| - | 2.828 | 3.578 | 4.000 | 3.578 | 2.828 | - |
| - | - | 2.530 | 2.667 | 2.530 | - | - |

Figure 4

METHOD AND APPARATUS FOR CALCULATING A LASER SHOT FILE FOR USE IN AN EXCIMER LASER

This is a continuation of U.S. patent application Ser. No. 12/375,428, filed on Apr. 21, 2009, and claims priority to PCT/EP07/57782, filed on Feb. 7, 2008.

FIELD OF THE INVENTION

The present invention relates to a method and apparatus for calculating a laser shot file for use in an excimer laser in particular using a dithering algorithm. The invention is specifically suitable for applying the laser shot file when performing a laser treatment of an eye or when producing a customized contact lens or an intraocular lens (IOL) by laser ablation.

DESCRIPTION OF THE RELATED ART

U.S. Pat. No. 6,090,100 relates to an excimer laser system for correction of vision with reduced thermal effects. It specifically relates to an apparatus and method for controlling the excimer laser system for removing tissue from the eye to perform various types of corrections, such as myopia, hyperopia, and astigmatism correction. In one disclosed embodiment, the excimer laser system provides a relatively large spot size which provides a relatively large coverage of treatment area per shot. While using such large spot sizes, the shots are generally not "adjacent" to each other but instead overlap to generate the desired degree of ablation at a particular point. For calculating the result of the overlapping shots, an algorithm is used. In one method of calculating treatment patterns using large, fixed spot sizes distributed throughout the treatment area, a dithering algorithm is used. Specific reference is made to a rectangular dithering, circular dithering and a line-by-line oriented dithering. Using any variety of shot dithering methods, an array of shots is created for a fixed spot size spread over a treatment area to correct to the desired degree of ablation. For the respective array, a grid is used with a constant grid width between individual grid positions. With the known dither methods, the shape of the desired ablation profile, which usually is a continuous profile, has to be transferred into a whole-numbered discrete density distribution. Here, the continuous profile represents a planned ablation and the whole-numbered discrete density distribution represents a series of ablating flying spot laser pulses. The residual structure, i.e., the difference between the planned and the achieved profile, has to be minimised. Exact solutions can principally be found numerically but not in a reasonable time. Therefore, for this purpose, dither algorithms are used. The profile is discretised on a given grid. Using a cost function or merit function the algorithm decides for each position of the grid whether to place a shot or not. For this decision, usually only a few neighboring positions of the grid are taken into account. This dither algorithm saves calculation time without the need that the real size of the spot is taken into account. It is sufficient to know the shot volume which is ablated with one laser shot. However, under certain conditions, the known dither algorithms produce artefacts in parts of the profile, e.g., in low-density regions where the next neighboring shot is too far away. Artefacts may also be produced in high-density regions where at nearly every position, a shot is placed. The positions with no shot also have too large a distance for the assumption that only a few neighbor positions are necessary.

As regards the general background of dithering algorithms, reference is made to U.S. Pat. No. 6,271,936 B1, which relates to the field of digital image processing. It particularly relates to a method for digitally multitoning a continuous-tone image using error diffusion, dithering and over-modulation methods. Reference is made to the problem that an artefact may occur like worms which are formed when the black or white output pixels appear to string together in an area that should be otherwise uniform. Wherein this U.S. patent gives a detailed description of these known methods, it is related to a completely different technical field. Among other differences, known laser printer systems are using a respective fixed resolution given as a number of dots per inch, i.e., a higher number of dots per inch results in a better resolution. Moreover, a known laser printer has no problem with overlapping and touching dots because this does not result in an additional blackening when hitting a point twice or more often. Rather, to produce an image, a certain local area of the image having a certain grey level can be created by applying a corresponding number of dots in this local area.

SUMMARY OF THE INVENTION

The object underlying the present invention is to provide a method and apparatus for calculating a laser shot file for use in a refractive excimer laser, wherein the difference between the planned and the achieved profile is minimised. This object is solved with the features of the claims.

A desired ablation profile for correcting for example myopia has a maximum shot density in the central part of the treatment zone whereas a minimum shot density is present along the circumferential border of the treatment zone. Thus, the number of laser shots to be applied to the central part of the treatment zone is higher than in other sub-areas in particular along the border of the treatment zone.

For the correction of, for example, hyperopia the minimum shot density is present in the central part of the treatment zone. On the other hand, the ablation profile requires a higher number of laser shots along a circumferential border of the treatment zone.

The invention is generally applicable for any ablation profile, wherein sub-areas having different shot densities are investigated in order to determine any sub-area having a maximum shot density and/or any sub-area having a minimum shot density.

The general concept of the present invention is based on the idea to adapt the dither algorithm which is used for placing laser shots of the excimer laser when discretizing a given ablation profile on a given grid. Using a cost function the dither algorithm decides for each position of a grid whether to place a shot. More specifically, the shot density for obtaining a predetermined desired ablation profile is calculated first. Depending on the calculated shot density of the desired ablation profile, the dither algorithm is adapted by using a dynamic threshold value being used in a cost function for the shot calculation.

According to a preferred embodiment of the present invention, the threshold value is selected from at least two different threshold values depending on the minimum shot density and/or maximum shot density of the desired ablation profile. Generally, for a desired ablation profile having low shot densities, a lower threshold value is used. For a desired ablation profile having high shot densities, a higher threshold value is used.

According to a preferred embodiment of the present invention, a first threshold value is a value within the range of 0% to 20% of the maximum shot density of the ablation profile. Alternatively or in addition a second threshold value is a value within the range of 20% to 80% of the maximum shot density. Alternatively or in addition a third threshold value is a value within the range of 80% to 100% of the maximum shot density.

According to a further preferred embodiment of the present invention, more than three different threshold values are used and more preferably the threshold value "TV(x, y)" is related to the shot density "D(x, y)" according to the following equation (1):

$$TV(x,y)=f(D(x,y)) \quad (1)$$

More preferably, there is a linear relationship between the threshold value "TV(x, y)" and "D(x, y)" according to the following equation (2):

$$TV(x,y)=a \cdot D(x,y) \quad (2),$$

wherein "a" is a positive factor within the range of $0 < a \leq 1.5$ and wherein "x" and "y" are the coordinates of the grid position for which the calculation is made.

Preferably, the threshold value is set for each grid position in correspondence to the density function. More preferably, the threshold value is set to a value equal to or nearby the value of the density function at a respective grid position.

The threshold value is preferably at least a value within the range of 80% to 110%, more preferably of 90% to 100% of the value of the density function at a respective grid position. Thus, the factor "a" of equation (1) is a value preferably within the range of 0.8 to 1.1, more preferably of 0.9 to 1.0. Best results can be achieved with a=1.

A local shot density D(x, y) within a sub-area around a grid position P(x, y) is calculated from an ablation profile z(x, y) within the respective sub-area using the ablation volume of a single laser shot $V_{shot}$ and a given width G using following equation:

$$D(x,y)=z(xy)*G^2/V_{Shot} \quad (3)$$

According to a preferred embodiment, a dither algorithm is used for calculating the placement of the laser shots of the excimer laser on grid positions. The dither algorithm is adapted to the desired ablation profile by determining the optimised grid width for the grid to be used for the dither algorithm. For a more detailed description of this aspect to optimize the grid width, reference is made to the co-pending patent application of the present applicant with the title "Method and apparatus for calculating a laser shot file for use in a refractive excimer laser".

According to a preferred embodiment, with following equation the grid width is found for a maximum value of the Profile $z_{max}(x, y)$ and for a desired maximum density $D_{max}(x, y)$:

$$G=\sqrt{V_{shot}*D_{max}(x,y)/z_{max}(x,y)} \quad (4)$$

With equation 3 the local shot density around the minimum of the desired profile is calculated with a given grid width. Preferably the grid width is calculated with equation 4. The influence of the dynamic threshold is explained using two examples. As a first example a treatment using a treatment zone of about 5.5 mm for a desired correction of +4 dpt is selected. This hyperopia correction has the maximum of the ablation along an annular portion circumfering the centre. The desired depth is approximately 26 µm. About 445 laser shots are necessary to reach a result with a typical excimer treatment laser. To get shot densities along the annular portion of about 18% a grid width of 98 µm is chosen. In this example an ablation is calculated using a constant threshold. In a second example of an ablation the treatment zone is again 5.5 mm and the correction is +4 dpt. The desired maximum depth is also about 26 µm and about 445 laser shots are needed. For the second example, a dynamic threshold is used. The second example shows the advantage to use a dynamic threshold when calculating the ablation.

According to a further preferred embodiment, a desired ablation profile is divided into at least two ablation sub-profiles. Then for each ablation sub-profile, the respective shot density is calculated and a respective grid width based on the respective calculated density of the ablation sub-profile is determined. Each sub-profile is calculated using the dynamic threshold. Thus, for a desired ablation profile where the contrast is too high, i.e., a difference between the maximum shot density and the minimum shot density is too high, the calculation of the laser shot file is made in two or more runs preferably using different grid constants or grid widths for each respective ablation sub-profile resulting in a corresponding laser shot file. Thereafter, the two or more laser shot files can be combined in one single laser shot file.

According to the present invention, the calculated, placed laser shots are processed in a further step of sorting to obtain a laser shot sequence. The sorting is performed taking into consideration that any thermal effects should be avoided, i.e., two consecutive laser shots are preferably placed on different grid positions in the treatment zone which are at a distance from each other.

BRIEF DESCRIPTION OF THE DRAWINGS

FIG. 1A is a diagram showing the location of laser spots for a first test using a constant threshold value, FIG. 1B is a diagram showing the planned and the achieved profile as a cross-section along the horizontal axis of FIG. 1A, FIG. 1C is a diagram showing the planned and the achieved profile as a cross-section along the vertical axis of FIG. 1A, FIG. 2A is a diagram showing the location of laser spots for a second test using a dynamic threshold value according to a preferred embodiment of the present invention, FIG. 2B is a diagram showing the planned and the achieved profile as a cross-section along the horizontal axis of FIG. 2A, FIG. 2C is a diagram showing the planned and the achieved profile as a cross-section along the vertical axis of FIG. 2A, FIG. 4 shows an example of a sub-grid with weighting factors usable for weighting neighboring error values.

DETAILED DESCRIPTION OF THE PREFERRED EMBODIMENTS

Figure 3:
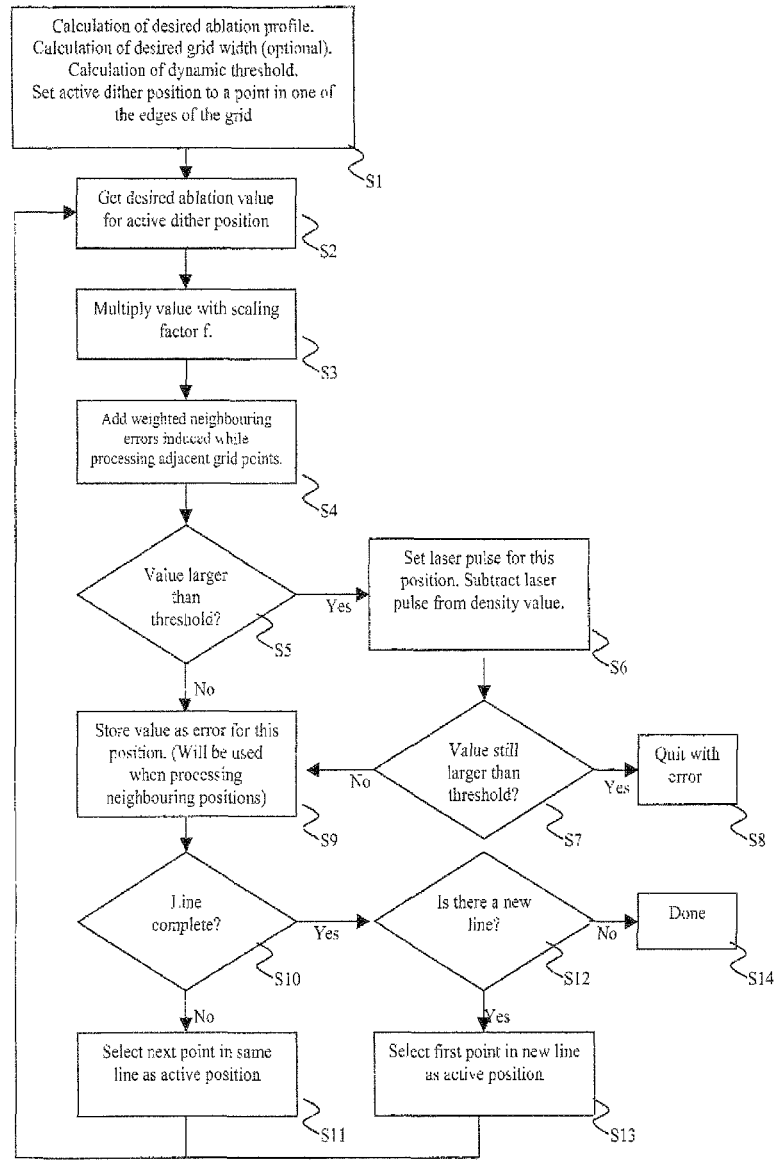
FIG. 3 shows a flow diagram with a calculation of laser pulse patterns with a dither algorithm.

FIGS. 1A, 1B and 1C show the simulated calculation of a laser shot file for use in an excimer laser for the correction of hyperopia with a value of about +4 dioptres, using a typical excimer laser for refractive treatments, within a treatment zone having a diameter of 5.5 mm and using a laser spot having a diameter of 1 mm. In this simulated first test, the grid width is 98 µm. Thus, the distance between two neighbor grid points is 98 µm. In this example, the grid points are arranged in rows and columns. In total, 445 laser shots are used for achieving the ablation. Depending on the ablated volume of a single shot the resulting treatment is expected to have a refraction of said about +4 dioptres. The diagram of FIG. 1A shows the respective centre position of each of the 445 laser shots which is related to one of the grid positions each marked with a "+"-sign. In the upper right corner of FIG. 1A, the grid is schematically shown having a grid width of 98 μm. Each of the shown laser shot centre positions are arranged on a grid point of this grid. The diagram of FIG. 1B shows, as a dashed line, the desired ablation profile, i.e., the ablation depth in μm with respect to a respective X-position. The ablation depth is approximately 26 μm in an annular portion of the treatment zone at about the x-positions −2 and +2 and is smaller in the centre portion and at both sides. The ablation depth is almost zero in the centre portion. It further shows the simulated resulting ablation profile as a continuous line as a cross-section taken along the horizontal axis through the point 0-0 in FIG. 1A. Similarly, FIG. 1C shows the desired ablation profile as a dashed line which is taken as a cross-section along the vertical axis through the point 0-0 in FIG. 1A. FIG. 1C further shows the resulting ablation profile as a continuous line taken as a cross-section along the vertical axis through point 0-0 of FIG. 1 A. In FIG. 1 the average shot density inside the treatment zone, having in this example a diameter of 5.5 mm, is about 18% (FIG. 1A). The respective centre positions of the laser shots are placed within a range of ±2.7 mm in the X-direction and ±2.7 mm in the Y-direction.

FIGS. 2A, 2B and 2C show the results of a similar second test as in FIGS. 1A, 1B and 1C except for using a dynamic threshold. More specifically in this test the shot density D (x, y) has been used as the threshold value TV (x, y). Thus, the factor "a" in the above equation (2) is selected as a=1.

The use of a constant threshold value for the first test causes artefacts like the linewise arrangement of laser shot positions in the lower part of the ablation (FIG. 1A). For example, as shown, several laser shots are provided at grid positions which are arranged along a horizontal bottom line at a closer distance. Further laser shots are provided at grid positions which are arranged at a larger distance from this horizontal bottom line. Thus, the laser shots are not provided in an equal manner resulting in a deviation from the desired ablation profile (see FIG. 1C).

A comparison of the Figures for the first test and the second test shows that the resulting ablation profile in the second test is better, i.e., the curve of the resulting ablation profile better follows to the curve of the desired ablation profile (see FIGS. 2B and 2C). In particular, FIG. 1C shows that the resulting ablation profile deviates from the desired ablation profile, i.e., there is a shift with respect to the right part of the desired ablation profile. The dither algorithm produces artefacts in parts of the resulting ablation profile which may depend on the order of the calculation of the laser shots for respective grid positions. In regions with gradients in shot density, the shots are shifted. The shift depends on the depth of the desired ablation. Additionally, artefacts called worms may be introduced.

By using a dither algorithm, the input parameters are the shot volume of a laser shot and the desired ablation profile. There is no need to take the beam diameter into account as the dither algorithm works independently therefrom. The dither algorithm provides a laser shot file as an output. More specifically, the dither algorithm is used for the placement of laser shots of the excimer laser on grid positions. Preferably, a cost function is used for deciding for each grid position whether a laser shot is placed or not. Herein, preferably the decision is made with regard to whether one or more laser shot(s) is (are) placed at a grid position(s) within the neighborhood of the given grid position. Preferably, a dither algorithm is used as disclosed in U.S. Pat. No. 6,090,100.

In the following a preferred dithering algorithm will be described with reference to FIG. 3 which shows a flow chart representing an example for the error diffusion. This dither algorithm is based on the concept of error diffusion. Prior to the step of error diffusion, the desired ablation profile is calculated based, e.g., on the desired correction of a patient's eye or the modification of contact lenses or of IOLs. This profile is stored within a grid having a specific grid width. For example, such a grid has 256×256 values which covers an area of $15^2$ mm$^2$. The error diffusion may be started in one edge within that grid and follows it line by line.

In a first step S1, the ablation profile and the dynamic threshold is determined using equation 1 and the active dither position is set to a point in one of the edges of the grid. Optionally, a desired grid width is calculated. Said active dither position represents the actual position within the grid being processed.

In a next step S2, a desired ablation value for the active dither position is obtained. In step S3 this desired ablation value is multiplied with a scaling factor f. The scaling factor f takes into account the different size of laser pulse and the positioning step, i.e., the grid width. More specifically, the scaling factor is calculated as follows to get the desired shot density at this position (see equation 3):

$$f = \frac{\text{(Grid width)}}{V\_shot}$$

For the above-mentioned grid having 256×256 values covering an area of $15^2$ mm$^2$, the grid width is 15 mm/256=58 μm. Thus, the area of the smallest square the laser beam can be sent around is $(58 \, \mu m)^2$. Thus, the number of calculated pulses are reduced in order to take into account for the overlapping of laser pulses.

In a next step S4, weighted neighboring errors are added to the scaled desired ablation value for the active dither position. These weighted neighboring errors are preferably the weighted sum of errors of adjacent grid points that have already been processed. An example will be described later.

In a further step S5, a decision is made whether the obtained value is larger than a predetermined threshold. Thus, the sum of the value for the respective grid point and the weighted errors of adjacent grid points will be compared to this threshold value. If the value is not larger than the dynamic threshold T (x, y) step S9 follows. If the value is larger than the threshold, a laser pulse is set for this grid position in step S6. One laser pulse is subtracted from said density value. Then in step S7 it is determined whether a new value is still larger than the threshold. In case the new value is larger than the dynamic threshold in step S8, it is determined that an error of shot overflow occurred. In other words, if at a grid position it would be necessary to set more than laser pulse, the algorithm has to stop with an error. By the use of grid width calculated with equation 4 this error can be avoided. In this exemplary implementation of the error diffusion, a maximum of one laser pulse for each grid position is allowed.

On the other hand, if the new value is not larger than a dynamic threshold in step S9, this new value is stored as an error for this particular grid position. It will be used when processing neighboring positions for the calculation with respect to further dither positions.

In the next step S10, it is decided whether the line is complete; if not, in step S11 a next point in the same line is selected as an active position and the before-mentioned processing is repeated. In case the line is complete, then in step S12 a decision has to be made whether there is a new line; if yes, then in step S13 a first point in the new line is selected as active position and the processing is repeated. Otherwise, if there is no new line, the processing ends with step S14. The before-mentioned grid point error represents the ablation error done at a particular grid point. For each grid point processed, this error is the sum of desired ablation value plus the weighted neighboring errors minus the laser pulse ablation depth (if a laser pulse has been set for that position).

FIG. 4 shows an example for weighting of errors of neighboring grid points. More specifically, FIG. 4 shows a sub-grid of 7×7 grid points, wherein the active dither position is shown in the middle. In this case, the weighting function is determined as 8/distance with a distance measured in units of grid points. The sum of the errors will then be normalised by a division with 70.736 which is the sum of all weighting factors used. As apparent from FIG. 4, the white positions indicate grid position not yet processed. Thus, before deciding whether a laser pulse has to be set at a given grid position, the error induced while processing adjacent grid points has to be added to the theoretical ablation value for that grid point. The errors of the neighboring grid points are not simply added but weighted due to their distance to the active grid point. The respective weighting factors are shown in FIG. 4. It shall be noted that this is just one possible method for summing up the surrounding errors, which is working fine.

It shall be noted that the above described dither algorithm is only one example for using the present invention.

A laser shot sequence may be determined thereafter by using a separate sorting algorithm. A sorting may be performed in order to avoid thermal effects. Thus, any two following laser shots should preferably be placed at two grid positions at a distance from each other. Preferably, every four shots a laser shot is placed in the same region as the first shot.

The foregoing disclosure and description of the invention are illustrative and explanatory thereof and changes in the construction and method of operation may be made without departing from the scope of the invention.

What is claimed is:

1. An apparatus for calculating a laser shot file for use in an excimer laser for performing a refractive laser treatment of an eye or for producing a customized contact lens or an intraocular lens, the apparatus comprising:
   a computer system configured to receive information with respect to a desired ablation profile and implement a dither algorithm,
   wherein the dither algorithm is adapted to the desired ablation profile by using a dynamic threshold depending on the shot density of the desired ablation profile for calculating the laser shot file.

2. The apparatus of claim 1, wherein the computer system is configured to discretize the desired ablation profile on a given grid when implementing the dither algorithm and decide for each grid position whether to place a laser shot of the excimer laser on said grid position.

3. The apparatus of claim 2, wherein the dither algorithm is using a cost function for determining for each grid position whether to place a laser shot of the excimer laser on said grid position.

4. The apparatus of claim 2, wherein the computer system is configured to decide whether to place a shot on a given grid position using information regarding a corresponding decision with regard to grid positions in the neighborhood of the given grid position.

5. The apparatus of claim 2, wherein the computer system is configured to sort the placed laser shots.

6. The apparatus of claim 1 wherein the computer system is configured to calculate a shot density for obtaining the desired ablation profile,
   wherein said dynamic threshold is defined depending on the calculated shot density of the desired ablation profile.

7. The apparatus of claim 1, wherein the computer system is configured to select at least two different threshold values depending on the desired ablation profile.

8. The apparatus of claim 7, wherein a first threshold value is selected for a desired ablation profile having low shot densities and/or a second threshold value is selected for a desired ablation profile having high shot densities, wherein said first threshold value is lower than said second threshold value.

9. The apparatus of claim 7, wherein the first threshold value is a value within a range of 0% to 20% of a maximum shot density of the desired ablation profile and/or the second threshold value is a value within a range of 20% to 80% of the maximum shot density and/or a third threshold value is a value within a range of 80% to 100% of the maximum shot density.

10. The apparatus of claim 1, wherein the computer system is configured to determine the threshold value $TV(x, y)$ in relation to the shot density of the desired ablation profile $D(x, y)$ according to the equation:

$$TV(x,y)=f(D(x,y)).$$

11. The apparatus of claim 1, further comprising:
   means for determining the threshold value $TV(x, y)$ as a linear relationship to the shot density of the desired ablation profile $D(x, y)$ according to the following equation:

$$TV(x,y)=a \cdot D(x,y),$$

wherein a is a factor greater than zero and less than or equal to 1.5.

12. The apparatus of claim 11, further comprising:
   means for setting the threshold value to a value equal or nearby the value of the shot density.

13. The apparatus of claim 1, wherein the computer system is configured to determine a grid width of the given grid based on the calculated shot density of the desired ablation profile.

14. The apparatus of claim 1 wherein the computer system is configured to divide a desired ablation profile into at least two ablation sub-profiles, calculate the shot density of each of said ablation sub-profiles, and determine a respective grid width based on the respective calculated shot density of each of the ablation sub-profiles.

15. The apparatus of claim 1, wherein the excimer laser provides a laser beam at a spot size fixed between 0.5 mm and 3.5 mm in diameter.

* * * * *